United States Patent [19]
Porter

[11] Patent Number: 6,093,191
[45] Date of Patent: Jul. 25, 2000

[54] FLOW-AROUND VALVE WITH CONTOURED FIXATION BALLOON

[75] Inventor: Christopher H. Porter, Woodinville, Wash.

[73] Assignee: SRS Medical, Inc., Burlington, Mass.

[21] Appl. No.: 09/181,105

[22] Filed: Oct. 28, 1998

[51] Int. Cl.$^7$ .................................................. A61B 17/58
[52] U.S. Cl. ............................................................. 606/94
[58] Field of Search ...................................... 606/191, 192, 606/193, 194, 195, 197; 600/30, 31; 604/96, 101, 103

[56] References Cited

U.S. PATENT DOCUMENTS

| | | |
|---|---|---|
| 2,494,393 | 1/1950 | Lamson . |
| 3,583,391 | 6/1971 | Cox et al. . |
| 3,630,206 | 12/1971 | Gingold . |
| 3,750,194 | 8/1973 | Summers . |
| 3,769,981 | 11/1973 | McWhorter . |
| 3,841,304 | 10/1974 | Jones . |
| 3,908,635 | 9/1975 | Viek ........................................ 604/158 |
| 4,386,601 | 6/1983 | Trick . |
| 4,419,985 | 12/1983 | Trick . |
| 4,579,554 | 4/1986 | Glassman . |
| 4,822,333 | 4/1989 | Lavarenne . |
| 4,878,901 | 11/1989 | Sachse . |
| 4,932,938 | 6/1990 | Goldberg et al. .......................... 604/96 |
| 4,994,066 | 2/1991 | Voss . |
| 5,030,199 | 7/1991 | Barwick et al. . |
| 5,088,980 | 2/1992 | Leighton . |
| 5,090,424 | 2/1992 | Simon et al. . |
| 5,096,454 | 3/1992 | Samples . |
| 5,112,306 | 5/1992 | Burton et al. . |
| 5,114,398 | 5/1992 | Trick et al. . |
| 5,306,241 | 4/1994 | Samples .................................... 604/94 |
| 5,483,976 | 1/1996 | McLaughlin et al. . |
| 5,513,659 | 5/1996 | Buuck et al. . |
| 5,591,145 | 1/1997 | Sachse . |
| 5,701,916 | 12/1997 | Kulisz et al. . |
| 5,713,861 | 2/1998 | Vanarthos . |

FOREIGN PATENT DOCUMENTS

| | | |
|---|---|---|
| 0 265 207 | 10/1987 | European Pat. Off. . |
| 2 595 564 | 3/1986 | France . |
| WO 97/06758 | 2/1997 | WIPO . |

*Primary Examiner*—Michael Buiz
*Assistant Examiner*—Tan-Uyen T. Ho
*Attorney, Agent, or Firm*—Cesari and McKenna, LLP

[57] ABSTRACT

A urethral valve system includes a fixation balloon that is positioned in and contoured to the geometry of the bladder near the opening to the urethra. The fixation balloon, which is narrower at an end that is closest to the urethra and wider at an opposite end, includes a channel through which urine is directed to flow from the bladder to the urethra. A valve balloon is positioned in the channel and inflates to prevent urine flow through the channel and deflates to allow urine to flow around the balloon and out the end of the channel. The fixation balloon may be attached to a Foley-type catheter, with the catheter providing the channel through the balloon. The fixation balloon then acts as a shock absorber for the system by moving relative to the catheter in response to, for example, a contraction in the bladder. The catheter may contain lumens that provide access to the valve balloon and/or the fixation balloon. The fixation balloon is inserted in a deflated state and inflated to hold the system in place. The fixation balloon remains inflated with the valve balloon providing continence when it is in an inflated state and allowing voiding when it is in a deflated state. Only when the device is to be removed from the body is the fixation balloon deflated.

14 Claims, 10 Drawing Sheets

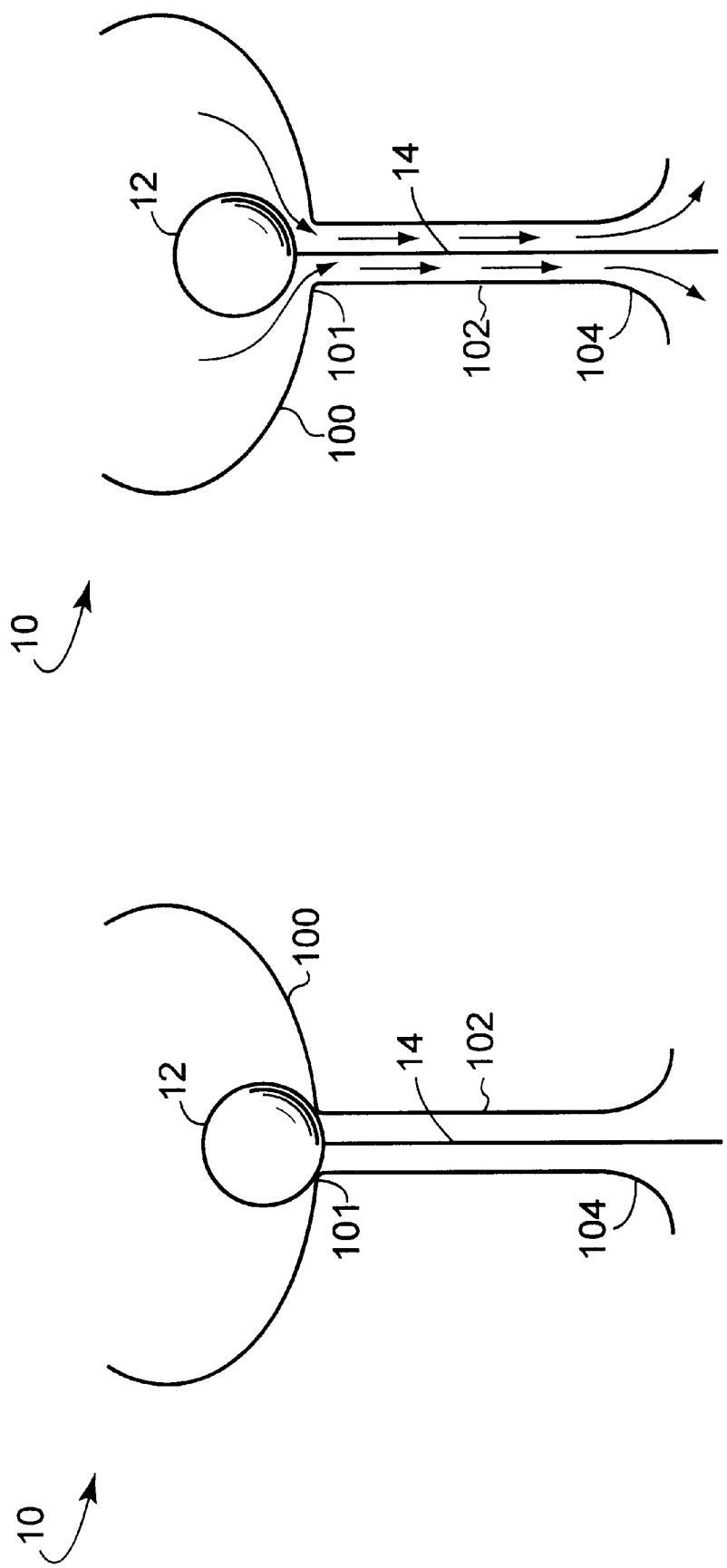

FLOW-AROUND VALVE WITH CONTOURED FIXATION BALLOON

FIELD OF THE INVENTION

This invention relates generally to devices that control incontinence and, more particularly, to urethral valves.

BACKGROUND OF THE INVENTION

Incontinence is a serious problem for many people and, in particular, for many females. Adult diapers may be used to capture leaking urine, or alternatively, urethral plugs or valves may be used to provide continence. Urethral plugs and values are positioned in the urethra to block urine flow. The plug is removed from the urethra for urination. The valve remains in place and opens to allow urine to flow through the valve, and out of the body.

The urethral plug is used once and then thrown away. After voiding, a new plug must be inserted to again provide continence. Over is time, with the repeated insertion and removal of the plugs, the lining of the urethra may become irritated.

Each time a plug is inserted, it carries bacteria from the meatus and the distal end of the urethra into the proximal end of the urethra. The bacteria may infect the urethra, particularly if the lining is irritated. Further, the bacteria may migrate up into and infect the bladder.

The urethral valve remains in the urethra over some period of days. The typical valve extends through the urethra to the outside of the body, where a mechanism for opening the valve is accessible to the user. The valve thus provides a path for bacteria to travel from the meatus and the distal end of the urethra to the proximal end of the urethra and the bladder. Further, the insertion of the valve into the urethra often irritates the lining of the urethra, and thus, promotes bacterial growth.

SUMMARY OF THE INVENTION

An improved urethral valve system includes a valve balloon that inflates to provide continence and in certain embodiments deflates to allow urine to flow around the balloon. A small-diameter catheter is attached to the balloon and extends through the urethra to provide access to the balloon from outside the body. When the urine flows around the balloon, the urine also flows around the catheter and through the urethra, and out of the body through the meatus. The urine cleanses the valve balloon, catheter and the urethra of bacteria, and thus, minimizes infection. In an alternative embodiment the valve balloon remains inflated during urination, and is moved from a position in which it blocks urine flow through the neck of the bladder to a position in which urine flows around the balloon, out of the neck of the bladder, around the catheter and through the urethra.

The valve system may be anchored in the bladder, to prevent the system from being drawn from the body by the flow of urine. The anchor may be, for example, a balloon, which may be either the same balloon that provides continence or a second balloon. If a single balloon is used both to anchor the system and provide continence, the balloon may deflate to a shape that retains the balloon in the bladder against the flow of urine. Alternatively, the system may include a mechanical means to hold the deflated balloon in the bladder, such as, for example, rubber fingers that extend from the base of the balloon beyond the neck of the bladder.

The valve balloon may instead be positioned within the urethra, with an anchoring mechanism positioned in the bladder to hold the deflated valve balloon in place during urination.

The catheter runs from the valve balloon through the urethra to the outside of the body, and includes a check valve at the end that is accessible to the user. To inflate the balloon, the user attaches to the check valve a small pump that supplies air or a liquid such as water to inflate the balloon. To deflate the balloon, the user manipulates the check valve to allow the water or air to drain from the balloon. The catheter has a small diameter, since urine flows around the catheter and not through it.

The valve system preferably includes an everting mechanism that provides non-irritating delivery of the valve and/or anchoring balloons to the body. An everted membrane unrolls to provide a path through the urethra for the balloons, to prevent irritation of the lining of the urethra. The everting mechanism also prevents bacteria from being drawn from the meatus and distal end of the urethra into the proximal end of the urethra and into the bladder.

BRIEF DESCRIPTION OF THE DRAWINGS

The invention description below refers to the accompanying drawings, of which:

FIG. 5A is an illustration of a fifth embodiment of a urethral valve system constructed in accordance with the invention;

FIG. 5B is an illustration of the fifth embodiment of the urethral valve system allowing urination;

DETAILED DESCRIPTION OF ILLUSTRATIVE EMBODIMENTS

Figure 1B:
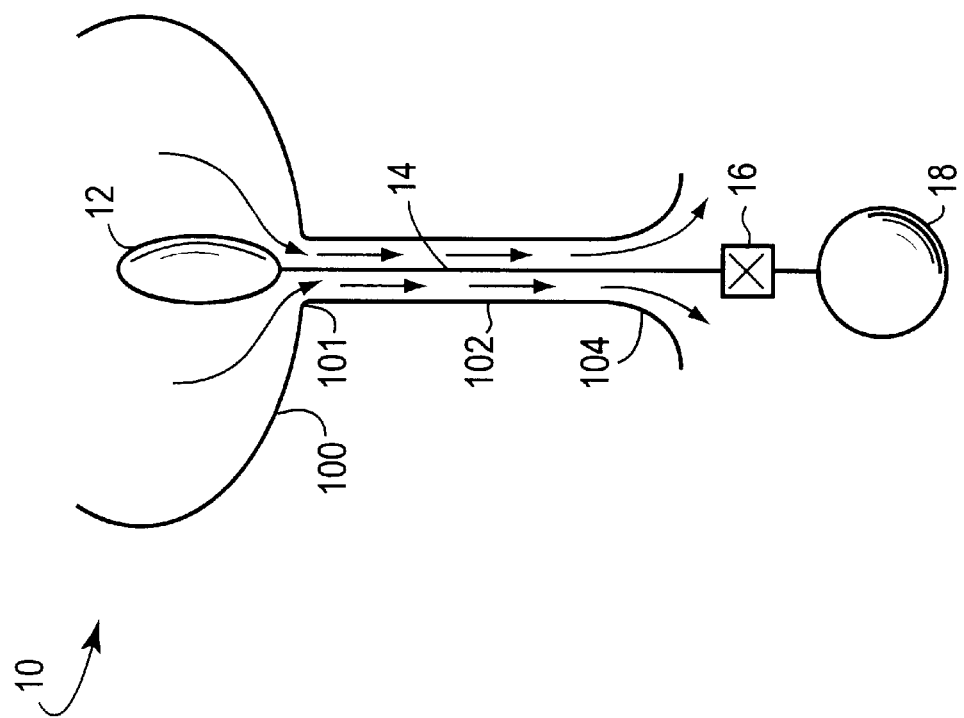
FIG. 1B is an illustration of the first embodiment of the urethral valve system allowing urination.
Figure 1A:
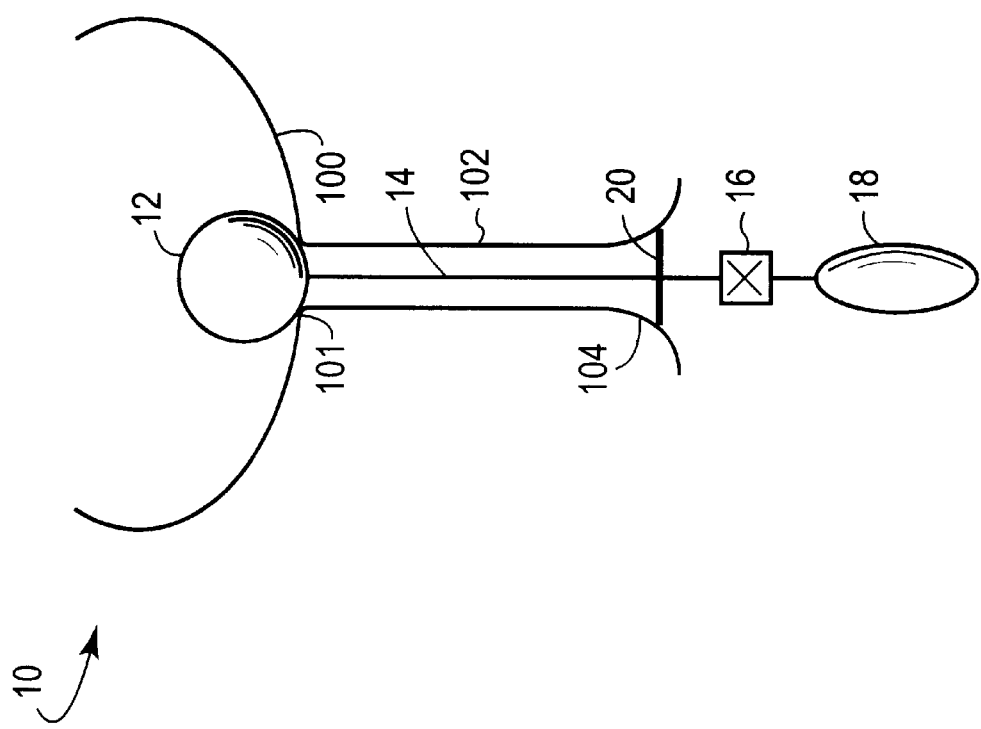
FIG. 1A is an illustration of a first embodiment of a urethral valve system constructed in accordance with the invention providing continence.

Referring to FIGS. 1A and 1B, a urethral valve system 10 includes a valve balloon 12 that is positioned in a bladder 100 to obstruct the flow of urine from the bladder. The diameter of the balloon 12 must be large enough essentially to seal the neck 101 of the bladder 100 and prevent urine flow from the bladder. A small-diameter catheter 14 attaches to the balloon 12 and extends through the urethra 102 and past the meatus 104. A check valve 16, which is closed to retain within the system the substance, such as air or water, that is used to inflate the balloon 12, extends slightly below the meatus 104. A pump 18, which is removably attached to the check valve 16, provides, for example, the water to the system. When the balloon is inflated, as depicted in FIG. 1A, the balloon provides continence.

For urination, a user deflates the balloon 12 through the check valve 16. As depicted by the arrows in FIG. 1B, when the balloon 12 is deflated urine flows around the balloon, through the neck 101 of the bladder 100, through the urethra 102 and around catheter 14, and out of the meatus 104. The urine flow cleanses the balloon 12 and the catheter 14 of bacteria in the same way that the body naturally cleanses the urethra, and thus minimizes the chances for infection from upwardly migrating bacteria.

The balloon 12 and the catheter 14 may also be coated with an antibacterial coating, to prevent colonization.

As depicted FIG. 1B, the pump 18 captures the water and retains it for use in re-inflating the balloon 12. The user may instead release the water from the system 10, and use fresh water to re-inflate the balloon.

The balloon is deflated for insertion into and removal from the bladder. Once deflated, the balloon is removed by gently pulling on the catheter 14.

For additional protection against the upward migration of both the system 10 and bacteria, a meatal collar 20 may be positioned slightly above the check valve 16. Further, the meatal collar 20, like the other system components, may be coated with an anti-bacterial coating to prevent colonization.

The balloon 12 and the catheter 14 may be made of any inflatable, non-reactive material, such as silicon. The catheter 14 has a small diameter since urine flows around the catheter rather than through the catheter.

Figure 2B:
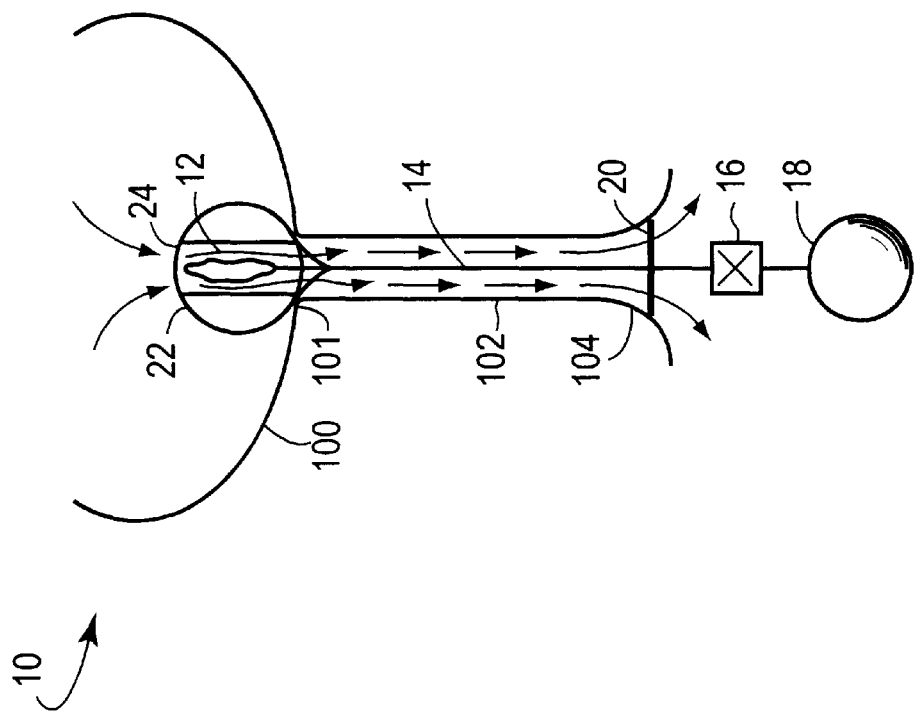
FIG. 2B is an illustration of the second embodiment of the urethral valve system allowing urination.
Figure 2A:
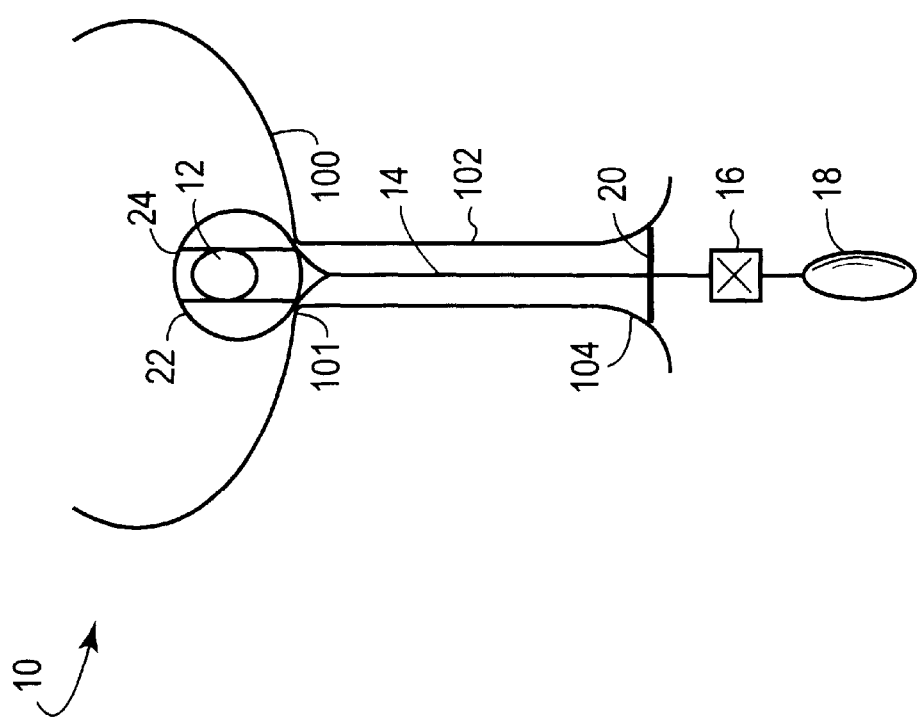
FIG. 2A is an illustration of a second embodiment of a urethral valve system constructed in accordance with the invention.
Figure 3B:
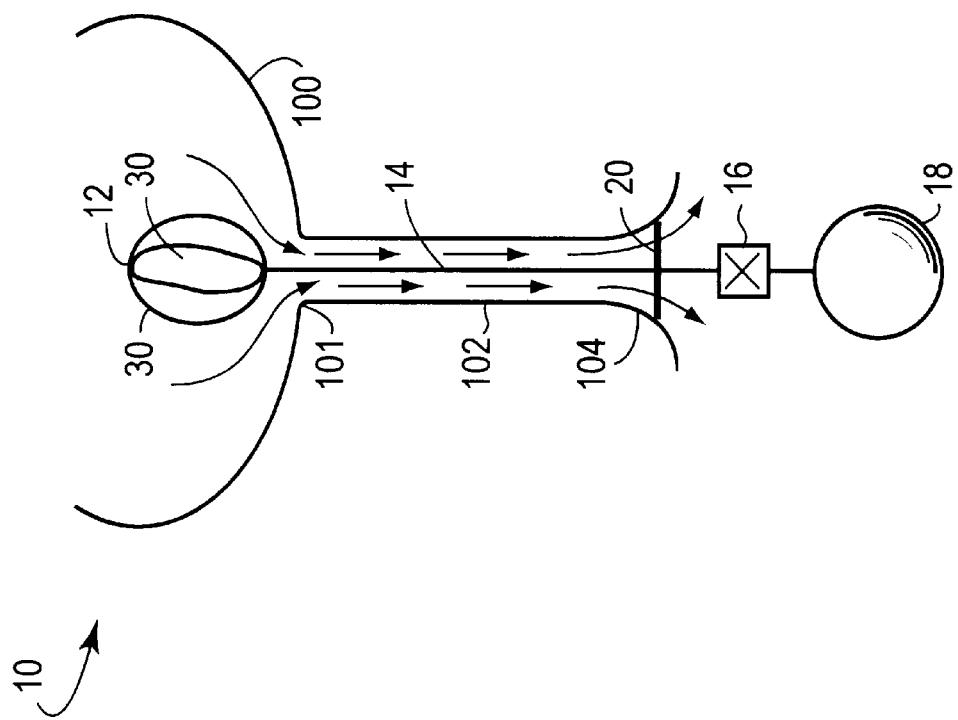
FIG. 3B is an illustration of the third embodiment of the urethral valve system allowing urination.
Figure 3A:
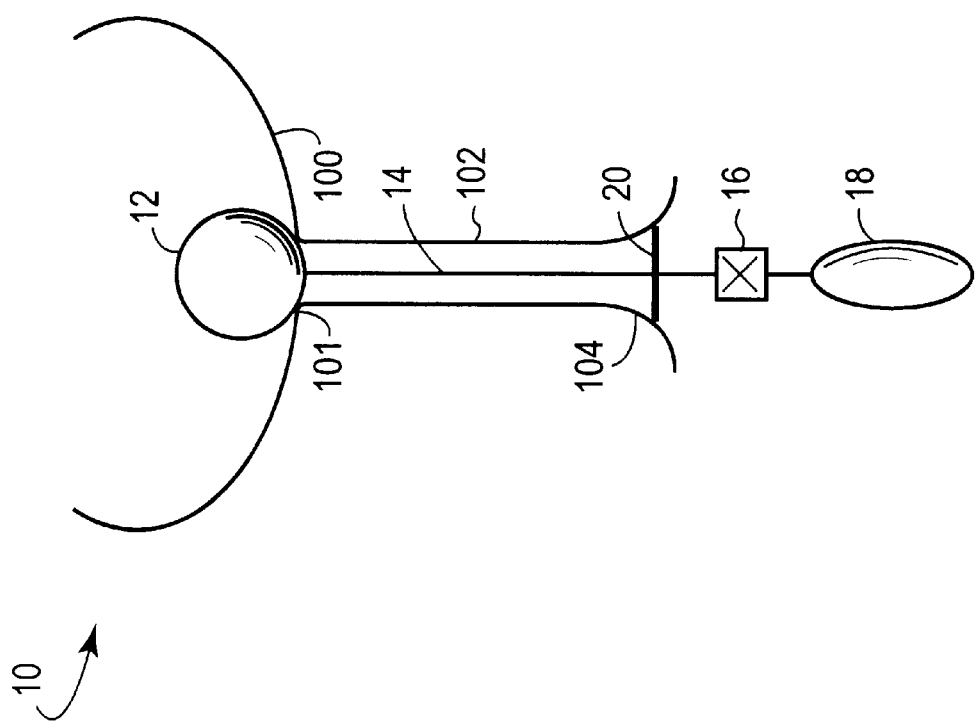
FIG. 3A is an illustration of a third embodiment of a urethral valve system constructed in accordance with the invention.
Figure 3D:
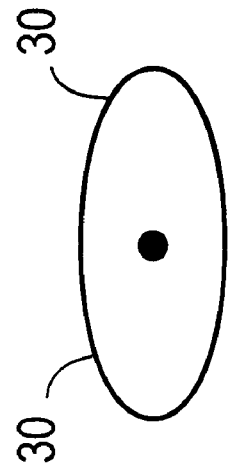
FIGS. 3C–D are top views of a component of the system of FIG. 3B.
Figure 3C:
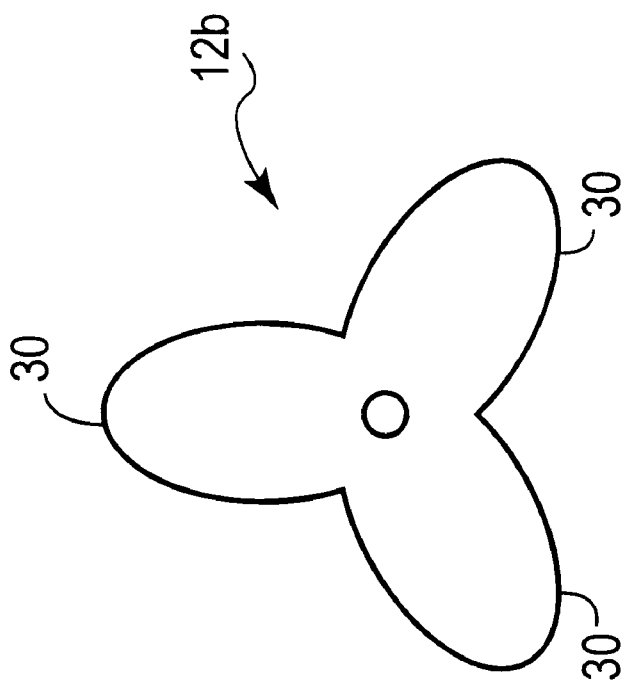

FIGS. 2A and 2B depict a second embodiment of the urethral valve system. In this embodiment, the valve balloon 12 is attached to a second, fixation balloon 22, which is included in the system to anchor it within the bladder 100. The fixation balloon in its inflated state, has a diameter that is larger than the neck 101 of the bladder 100, to ensure that the system will not be pulled from the bladder by the flow of urine. The fixation balloon 22 includes a channel 24 that houses the valve balloon 12. The valve balloon may be attached to the fixation balloon by, for example, webbing (not shown) through which urine can readily flow.

When the valve balloon 12 is inflated, the channel 24 is sealed to provide continence. When the valve balloon is deflated, as depicted in FIG. 2B, the channel 24 is opened and urine flows through the channel and around the valve balloon 12. The fixation balloon remains inflated during urination and holds the system in position against the flow of urine. As discussed above, the urine flow cleanses bacteria from the balloon 12 and the catheter 14, which comes in contact with the meatus 104 and the distal end of the urethra. The cleansing minimizes the upward migration of bacteria.

FIGS. 3A–3D depict a third embodiment of the urethral valve system. In this embodiment, the valve balloon 12 acts also as the anchoring mechanism. There is thus no need for the fixation balloon 22 (FIG. 2A). In this embodiment, the valve balloon 12 deflates into a shape 12b or 12c that includes one or more elongated arms 30. Urine can then flow around the arms 30, through the neck 101 of the bladder 100, around the catheter 14 and through the urethra 102, and out of the meatus 104.

The arms 30 have a span that is longer than the width of the neck 101 of the bladder 100, and they thus, retain the balloon 12 in the bladder against urine flow. The arms 30 are also flexible so that the balloon can be removed from the bladder by gently pulling on the catheter 14.

Figure 4B:
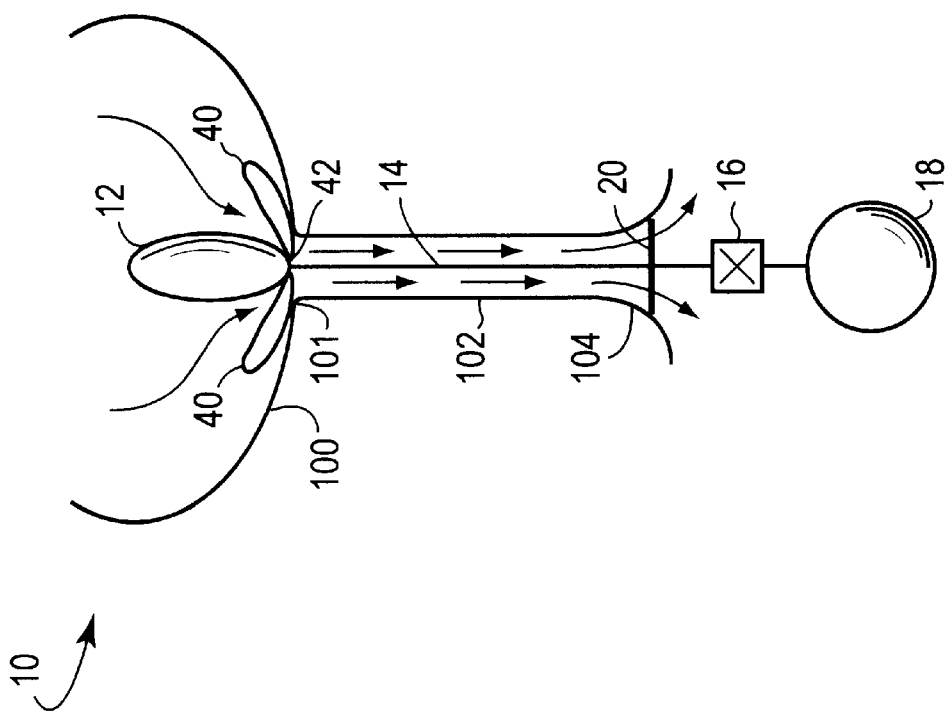
FIG. 4B is an illustration of the fourth embodiment of the urethral valve system allowing urination.
Figure 4A:
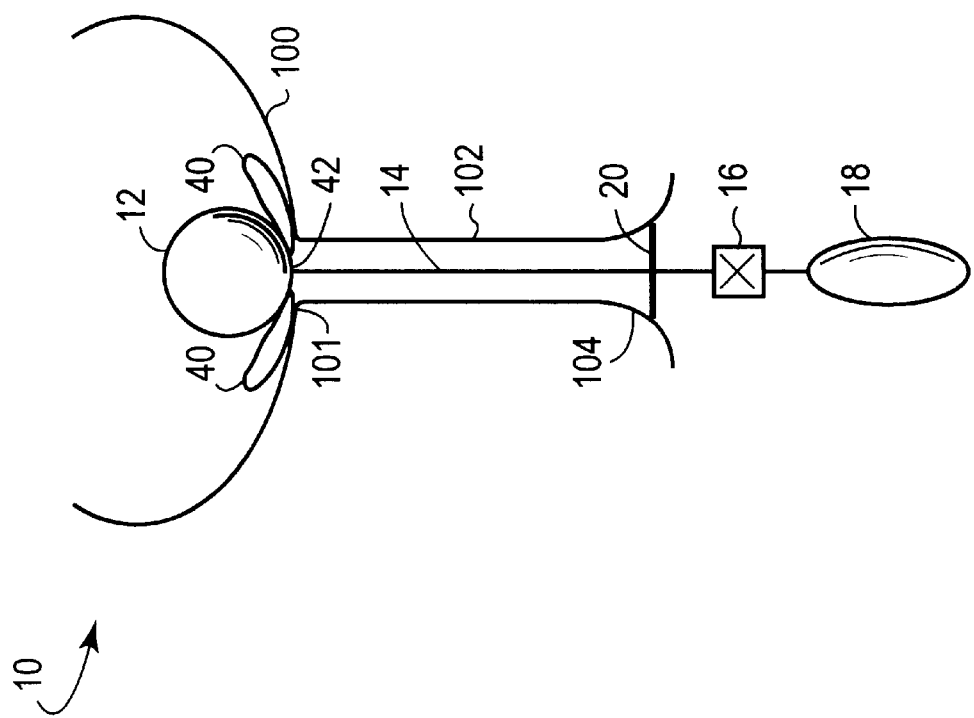
FIG. 4A is an illustration of a fourth embodiment of a urethral valve system constructed in accordance with the invention.

Referring now to FIG. 4, a fourth embodiment of the urethral valve system includes flexible fixation tabs 40 that extend outwardly from a base 42 of the balloon 12. When the balloon 12 is deflated, the tabs 40 hold the balloon in place at the neck 101 of the bladder 100. Urine then flows around the balloon and the tabs, out of the bladder, around the catheter 14 and through the urethra, and out of the body through the meatus.

In FIG. 5, the catheter 14 is stiffened somewhat, so that a user can move the valve balloon 12 away from the neck 101 of the bladder. Urine can then flow out of the neck of the bladder 100 and through the urethra 102. To reposition the valve balloon 12 in the neck of the bladder the user then gently pulls on the catheter 14.

Figure 6B:
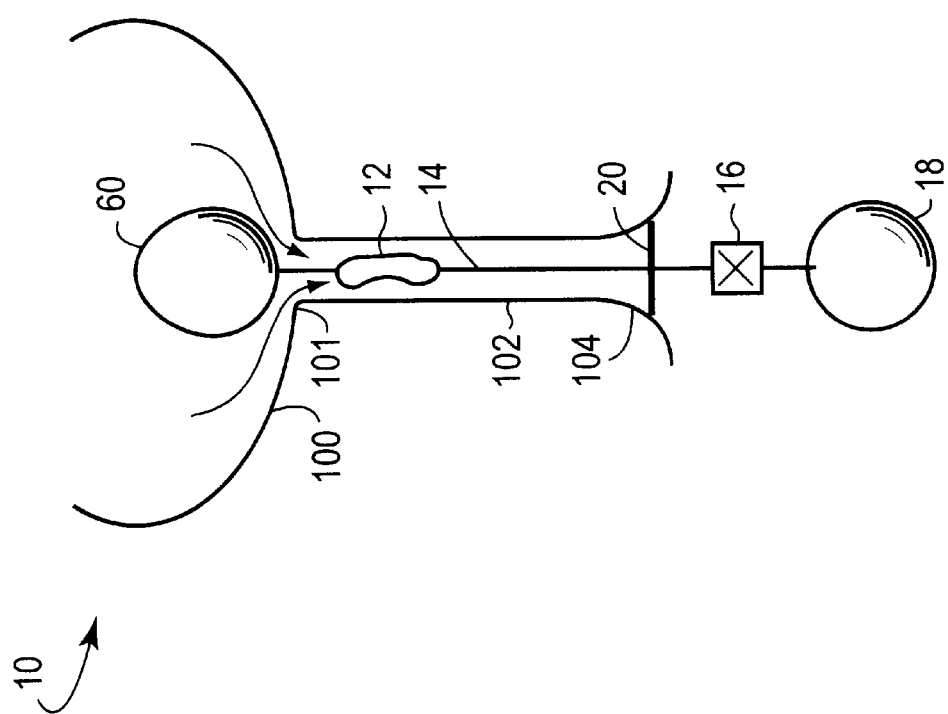
FIG. 6B is an illustration of the sixth embodiment of the urethral valve system allowing urination.
Figure 6A:
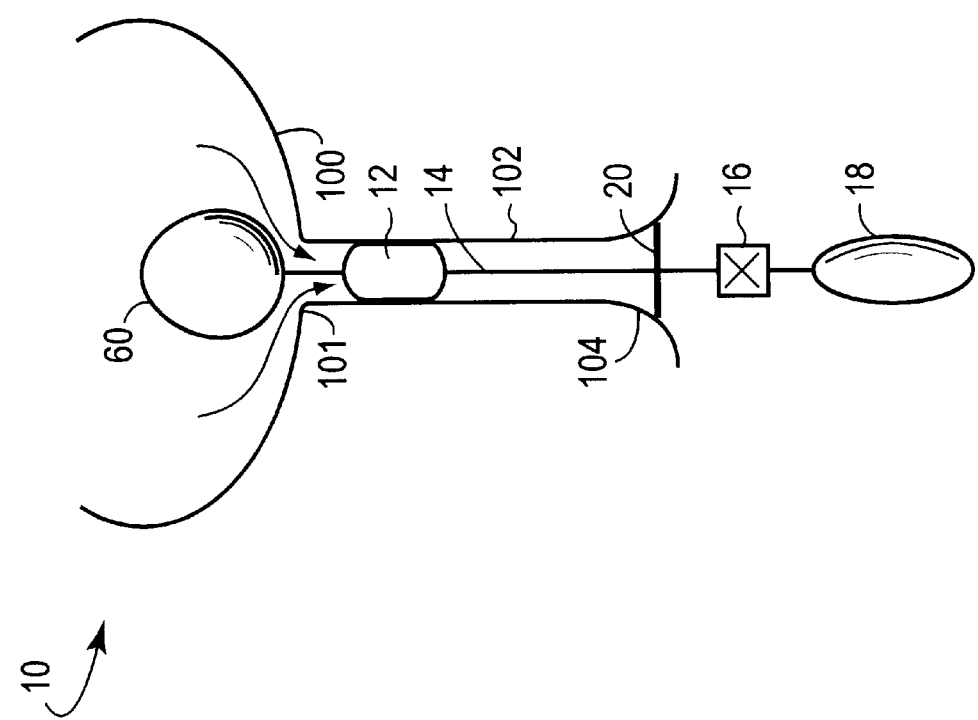
FIG. 6A is an illustration of a sixth embodiment of a urethral valve system constructed in accordance with the invention.
Figure 7:
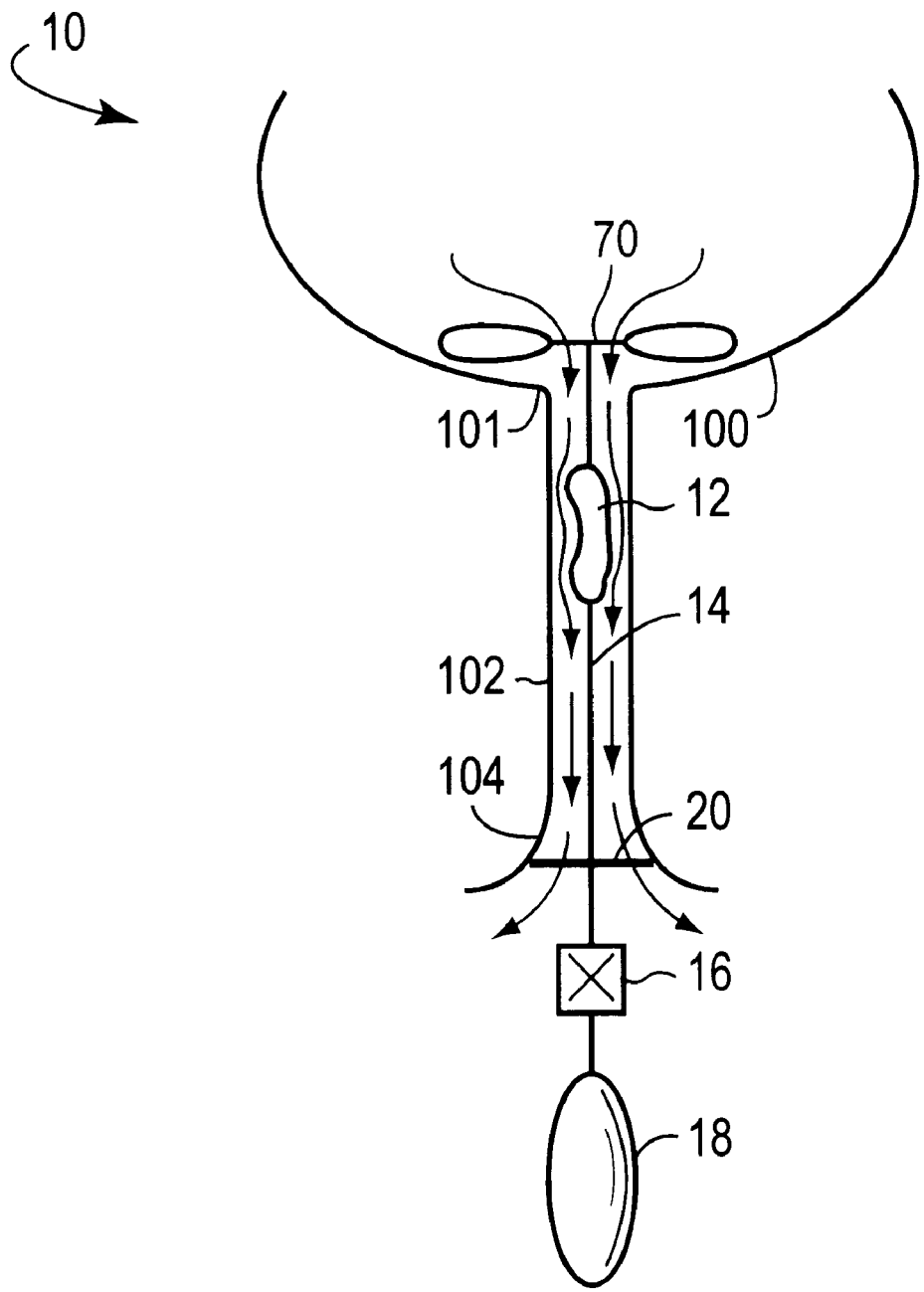
FIG. 7 is an illustration of a seventh embodiment of the urethral valve system allowing urination.

As shown in FIGS. 6 and 7, the valve balloon 12 may be positioned in the urethra 102. When the valve balloon 12 is inflated, it provides continence by blocking the flow of urine in the urethra. When the balloon 12 is deflated, urine flows around the balloon and the attached catheter 14 and through the distal end of the urethra 102 and out of the body through the meatus 104.

Different types of fixation devices may be used to retain the system in place against the flow of urine. For example, a second balloon 60 may be positioned in the bladder, as shown in FIG. 6. Alternatively, as depicted in FIG. 7, foldable arms 70, which are inserted and then unfolded in the bladder 100, may be used to anchor the system.

Figure 8:
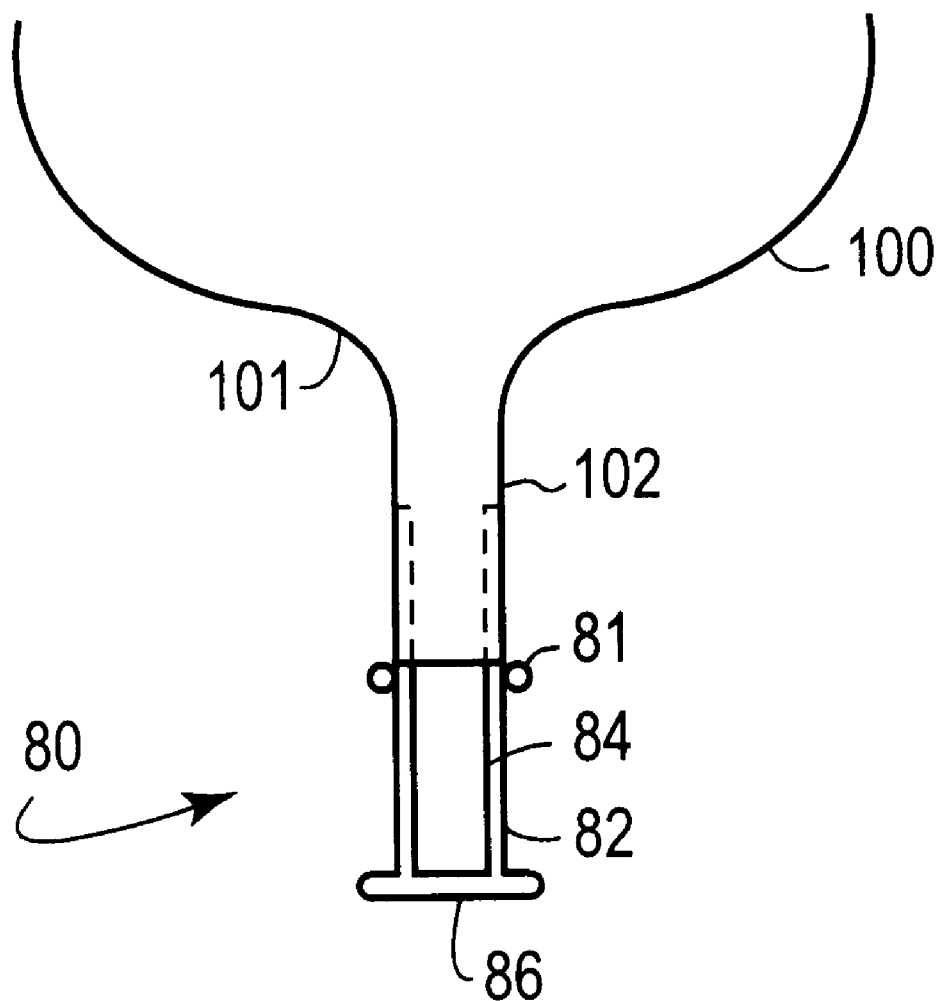
FIG. 8 is an illustration of an everting mechanism that may be used with the urethral valve system of FIGS. 1–7.

FIG. 8 depict s an everting mechanism 80 that may be used for introduction of the valve system 10 (FIGS. 1–7) into the body through the urethra. The everting mechanism 80 includes an introducing device 82, such as, for example, a tube, that a user inserts into the distal end of the urethra 102 up to a stop 81. The tube contains an everted membrane 84 with one end held by the stop. The membrane 84 unrolls, as depicted by dotted lines, as an advancing device 86 is pushed deeper into the urethra. The unrolled membrane then provides a pa th through which the valve system may be inserted, without coming into contact with the lining of the urethra. After the system is fully inserted, the membrane 84 is removed from the body.

There is essentially no relative motion between the membrane 84 and the walls of the urethra as the membrane unrolls. Accordingly, the lining of the urethra is not irritated by the insertion of the membrane, or the introduction of the valve system through the membrane.

Further, the surface of the membrane that comes in contact with the lining of the urethra does not come in contact with the distal end of the urethra. Accordingly, bacteria from the distal end of the urethra is not carried deeper into the urethra or into the bladder by either the membrane, or the valve system that is introduced through the membrane.

Figure 9:
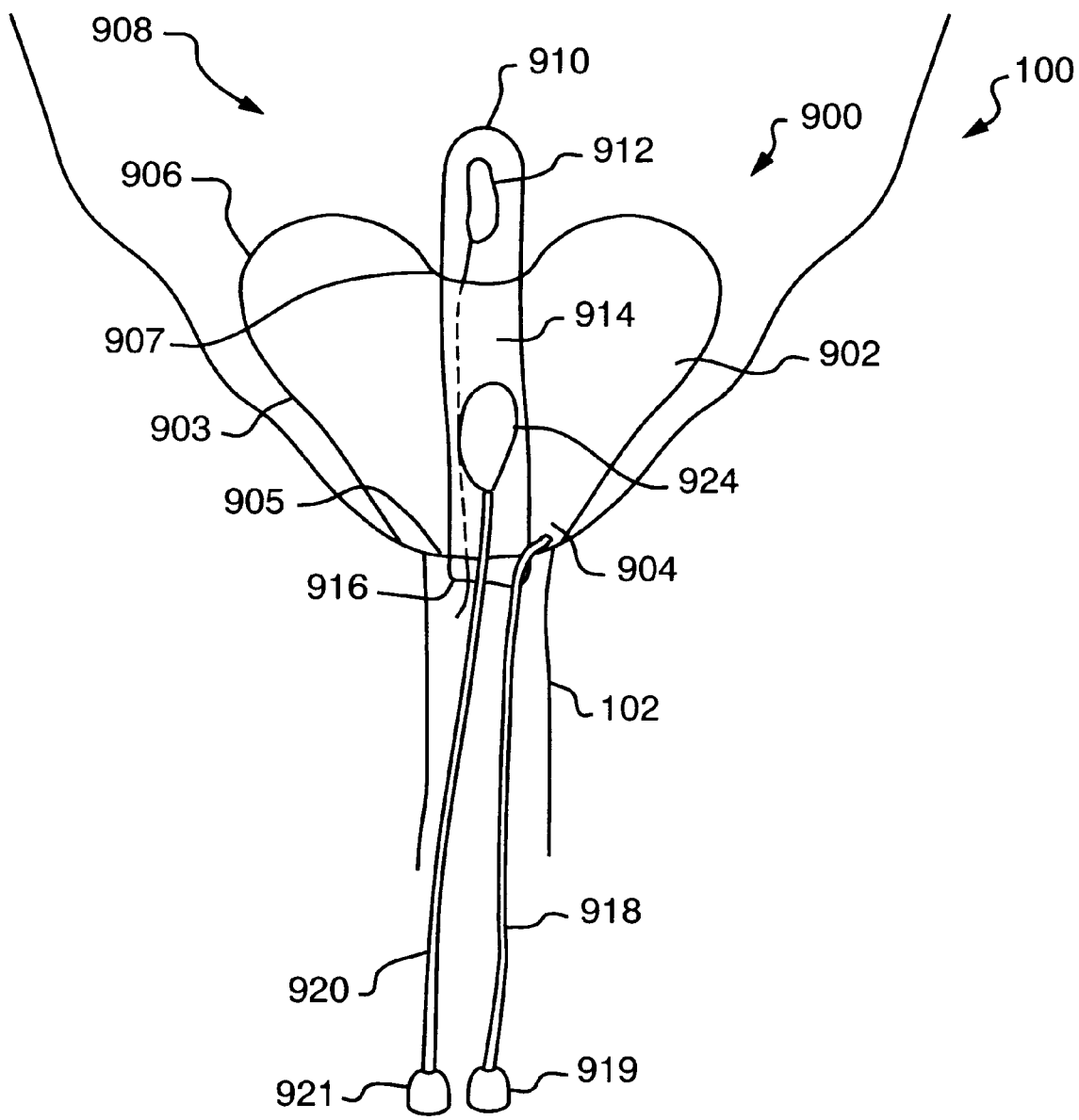
FIG. 9 is an alternative embodiment of the system of FIG. 2.

Referring now to FIG. 9, another embodiment 900 of the urethral valve system is depicted. In this embodiment, the fixation balloon 902 is contoured to the geometry of the bladder 100 near the opening to the urethra 102. The fixation balloon 902 is narrower on an end 904 that is closest to the urethra when the balloon is in place in the bladder, and wider on an opposite end 906. The fixation balloon thus provides a good seal at the bladder opening, and prevents urine from leaking around the balloon.

The contoured fixation balloon 902 is depicted in the drawing attached to an end 910 of a pliable Foley-type catheter 908. The catheter 908 has an opening 912 at the top end and a channel 914 through which urine flows out of the bladder. The arrows in the drawing indicate urine flow. An opposite end 916 of the channel 914 opens at the top end of the urethra. Urine thus flows out of the channel 914, into the urethra and around lumens 918 and 920 that extend through the urethra. The lumens, respectively, provide access to the fixation balloon 902 and to a valve balloon 924, which is positioned within the channel 914. The valve balloon 924 inflates to block urine flow through the channel 914, deflates to allow urine to flow through the channel and around the lumens, and then again inflates to block urine flow and provide continence. The fixation balloon 902 deflates for insertion and removal of the system, but otherwise remains inflated in the body. The balloons 902 and 924 are inflated and deflated through check valves 921 and 919.

The contoured fixation balloon 902, which is fixed to the catheter 908 at inside edges 905 and 907 of top and bottom ends 904 and 906, also acts as a shock absorber for the system 900. The fixation balloon moves at its outer edge 903 relative to the catheter 908 in response to, for example, a contraction in the bladder. The contoured fixation balloon can thus be comfortably worn by a user over an extended period of time, such as, for example, a day or a week.

As discussed with reference to FIG. 8, the system 900 preferably includes an everting mechanism, for ease of insertion.

The foregoing description has been limited to a specific embodiment of this invention. It will be apparent, however, that variations and modifications may be made to the invention, with the attainment of some or all of its advantages. Therefore, it is the object of the appended claims to cover all such variations and modifications as come within the true spirit and scope of the invention.

What is claimed is:

1. A urethral valve system for controlling urine flow from a bladder through a urethra, the valve system including:
    A. a fixation balloon for holding the system in position in the body, the fixation balloon having a shape that is contoured to the shape of the bladder at the entrance to the urethra and a channel through which urine flows, the fixation balloon preventing urine flow around the balloon;
    B. a valve balloon positioned in the channel to block urine flow through the channel when the valve balloon is inflated and allow urine to flow around the valve balloon and through the channel when the valve balloon is deflated;
    C. a catheter that attaches to the fixation balloon and provides access to the valve balloon from outside of the body for inflation and deflation of the valve balloon.

2. The urethral valve system of claim 1 wherein the catheter further provides access to the fixation balloon from outside the body for:
    i. inflating the fixation balloon after insertion, to hold the fixation balloon in the bladder, and
    ii. deflating the fixation balloon when the fixation balloon is to be removed from the body.

3. The urethral valve system of claim 1 wherein the catheter includes a first lumen to provide access to the valve balloon and a second lumen to provide access to the fixation balloon.

4. The urethral valve system of claim 1 further including an everting mechanism.

5. A fixation balloon for use in a device that is positioned in a bladder, the balloon including:
    A. a bottom end that, when the fixation balloon is inflated, has a diameter that is sized to an opening between the bladder and a urethra;
    B. a top end that, when the fixation balloon is inflated, has a larger diameter than the bottom end;
    C. sides that extend between the top and bottom ends, the sides being pliable; and
    D. said fixation balloon includes a channel through which urine is directed from the bladder;
the fixation balloon being shaped to the contours of the bladder at the opening to the urethra, wherein the channel may be blocked to provide continence and unblocked to allow urine to flow.

6. The fixation balloon of claim 5 wherein, when the balloon is inflated, the top end of the fixation balloon is sized to the geometry of the bladder above the opening to the urethra.

7. An incontinence device including:
    A. a fixation balloon that has a deflated state and an inflated state, the fixation balloon being positioned in the body in a deflated state and inflated to prevent urine flow around the balloon from a bladder, the fixation balloon being built in the shape of the bladder proximate to an opening between the bladder and a urethra and including a channel through which urine is directed from the bladder;
    B. a valve balloon that is positioned in the channel of the fixation balloon, the valve balloon having a deflated state to allow urine to flow around the balloon and through the channel and an inflated state to prevent urine flow through the channel.

8. The incontinence device of claim 6 wherein the fixation balloon is shaped to correspond to the shape of the bladder at an opening through which urine flows when the device is not in the body.

9. The incontinence device of claim 7 further including a catheter that provides access to the fixation balloon from outside the body.

10. The incontinence device of claim 7 further including a catheter with a first opening at a first end and a second opening at a second end, the catheter supporting the fixation balloon at the first end and providing the channel through the fixation balloon.

11. The incontinence device of claim 10 wherein the fixation balloon has a top end and a bottom end that are attached to the first end of the catheter, and when the fixation balloon is inflated the top end of the fixation balloon has a wider diameter than the bottom end of the fixation balloon.

12. The incontinence device of claim 11 wherein an outer perimeter of the balloon moves relative to the catheter.

13. The incontinence device of claim 10 wherein the catheter further provides access to the valve balloon from outside the body.

14. The incontinence device of claim 11 wherein the catheter includes a first lumen to provide access to the valve balloon and a second lumen to provide access to the fixation balloon.

* * * * *